United States Patent [19]

Leight et al.

[11] Patent Number: 4,490,857
[45] Date of Patent: Jan. 1, 1985

[54] BAND EARPLUG

[76] Inventors: Howard S. Leight, 3945 Ridgemont Dr., Malibu, Calif. 90265; Alan D. Rosen, 1243 Yale St. #8, Santa Monica, Calif. 90404

[21] Appl. No.: 433,735

[22] Filed: Oct. 12, 1982

[51] Int. Cl.³ .............................................. A42B 1/06
[52] U.S. Cl. .......................................... 2/209; 2/428; 128/152
[58] Field of Search ........................ 2/209, 423, 209.1; 128/152

[56] References Cited

U.S. PATENT DOCUMENTS

| Re. 29,487 | 12/1977 | Gardner, Jr. | 128/152 |
|---|---|---|---|
| 2,246,737 | 8/1939 | Knudsen | 128/152 |
| 3,259,128 | 7/1966 | Leight | 128/152 |
| 3,415,246 | 12/1968 | Hill | 2/209 |
| 3,565,069 | 2/1971 | Miller | 128/152 |
| 3,736,929 | 6/1973 | Mills | 128/152 |
| 3,800,791 | 4/1974 | Visor | 128/152 |
| 3,841,326 | 10/1974 | Leight | 2/423 |
| 3,856,007 | 12/1974 | Leight | 2/423 |
| 3,871,372 | 3/1975 | Bivins | 128/152 |
| 3,872,559 | 3/1975 | Leight | 128/152 |
| 3,881,570 | 5/1975 | Lewis | 128/152 |
| 4,023,642 | 5/1977 | Korn | 2/209 |

Primary Examiner—Henry S. Jaudon
Assistant Examiner—Mary A. Ellis
Attorney, Agent, or Firm—Freilich, Hornbaker, Rosen & Fernandez

[57] ABSTRACT

An ear noise protector apparatus is described, which provides a high level of noise protection, can be worn comfortably, and is economical to use. The apparatus includes a resilient head band with ear protector holders at either end, and a pair of ear protectors that are detachably mounted to the holders. Each ear protector includes a cap of slow recovery resilient deformable material, with a tapered central projection that can be received in the end of an ear canal, and an outer dish-shaped portion that can fit against the ear walls that surround the opening to the ear canal. The head band supplies sufficient force to maintain the cap in a deformed state wherein it conforms to the ear portion that surrounds the ear canal, to form a good seal therewith after being pressed firmly in place.

4 Claims, 5 Drawing Figures

BAND EARPLUG

BACKGROUND OF THE INVENTION

One type of earplug, or ear protector, is inserted deeply into the ear canal and is held in place by friction with the surface of the ear canal. An effective earplug of this type, described in U.S. Pat. No. Re. 29,487, consists of a cylinder of slow recovery resilient material. Such a plug is used by compressing it to a small diameter in the hand for easy insertion in the ear canal, where it expands for a good fit. However, many people are reluctant to insert devices deeply into their ears.

Another type of ear protector apparatus includes a headband that presses a pair of earplugs into the outer end of the ear canal. This can avoid the discomfort and hesitancy of some poeple to insert devices deeply into the ear canal. However, it is difficult to provide good noise attenuation and comfort with a headband protector. If only a small inward force is applied by the headband then the sound sealing is not as good as for the deeply inserted ear plugs; on the other hand, if a large inward force is continually applied by the headband then the device is uncomfortable. A headband type ear protector which provided large noise attenuation without the necessity of continually applying large inward forces against the ear of the wearer, would have wide applications.

SUMMARY OF THE INVENTION

In accordance with one embodiment of the present invention, an ear protector apparatus is provided, of the headband type, which provides very high noise attenuation. The apparatus includes a cap formed of foam plastic, which has a dish-shaped outer portion and a tapered protuberance projecting from the convex face of the dish-shaped outer portion to fit into the ear canal. The cap is supported on a headband that presses the protuberance into the end of the ear canal, and presses the outer portion against the walls of the ear that surround the ear canal. The cap can be formed of a soft or slow recovery resilient deformable material, so that it can deform closely against the walls of the ear to effectively block noise therefrom.

The slow recovery material can be of moderate stiffness, which has been found especially effective in blocking noise, even though the force applied by the headband is not sufficient to fully seat the cap against the ear. The wearer can initially press the ends of the ear band and the caps thereon against his ear to seat them, and the headband applies enough force to retain the seating configuration of the already-deformed caps to maintain a good sound-tight seal against the ear.

The caps can be held to the band by a rod-like coupling with an end nearest the cap formed of soft foam material that permits the cap to tilt slightly to fit close against the ear.

The novel features of the invention are set forth with particularity in the appended claims. The invention will be best understood from the following description when read in conjunction with the accompanying drawings.

DESCRIPTION OF THE PREFERRED EMBODIMENT

Figure 1:
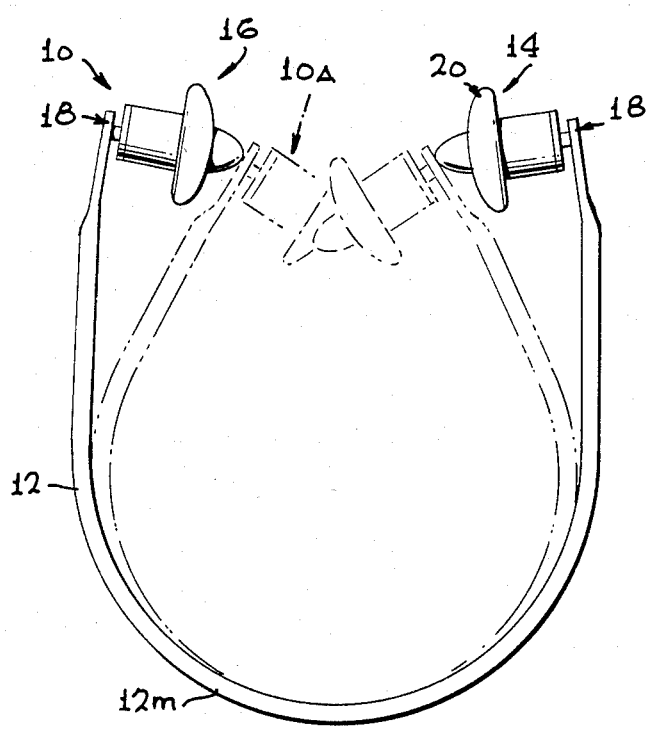
FIG. 1 is a front elevation view of an ear protector apparatus constructed in accordance with the present invention, showing its use configuration in solid lines, and its stored configuration in phantom lines.
Figure 2:
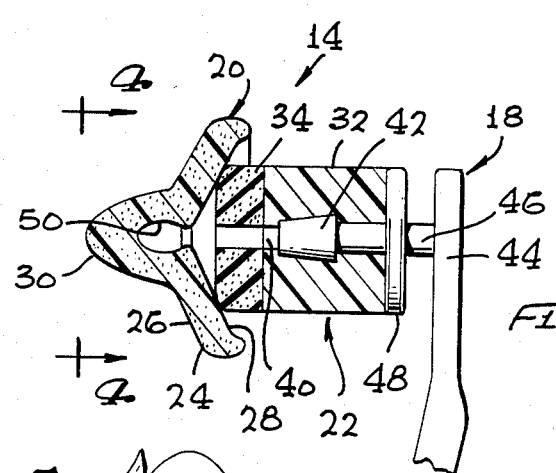
FIG. 2 is a partial perspective view of the apparatus of FIG. 1.

FIG. 1 shows an ear protector apparatus 10, which includes a headband 12 that can be worn around the head such as under the chin, and a pair of ear protectors 14, 16 attached to opposite ends 18 of the headband. The apparatus is initially stored in the position 10A, but the ends of the resilient band can be pulled apart to fit around the head and then released so that caps 20 of the ear protectors can fit against the ears of a wearer to block sound.

Figure 3:
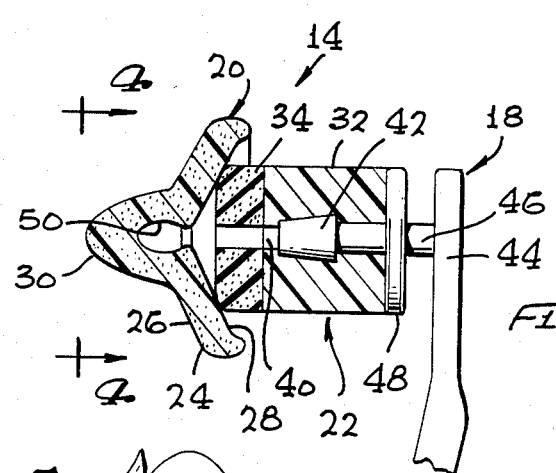
FIG. 3 is a sectional view of the apparatus of FIG. 2.
Figure 5:
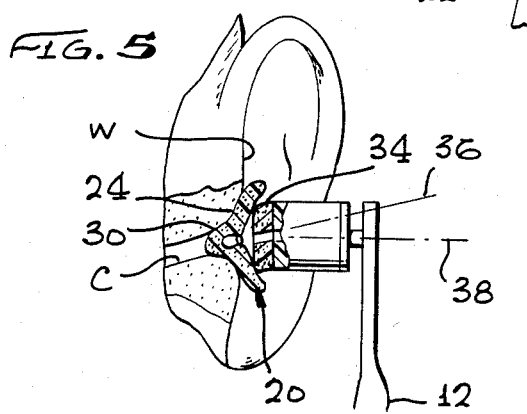
FIG. 5 is a partial sectional view of the apparatus of FIG. 3, shown applied to an ear.
Figure 4:
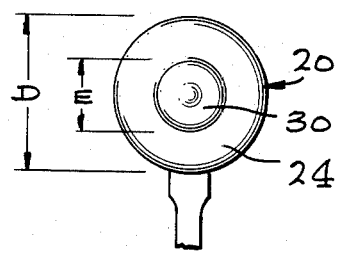
FIG. 4 is a view taken on the line 4—4 of FIG. 3.

As shown in FIG. 3, the ear protector 14 includes a coupling 22 which lies between the headband 18 and the cap 20. The cap 20 includes a dish-shaped outer portion 24 with convex and concave faces 26, 28, and a tapered protuberance 30 extending from the middle of the convex side of the dish-shaped outer portion. The protuberance 30 is designed to fit into the outer end of the ear canal. The dish-shaped outer portion 24 of the cap is designed to fit against the ear walls that surround the opening to the ear canal. FIG. 5 shows the ear protector 14 applied to a human ear, with the protuberance 30 lying in the outer portion of the ear canal C and with the outer portion 24 of the cap lying against the ear walls W at the portion thereof that surrounds and forms the entrance to the outer end of the ear canal.

The cap 20 is preferably formed of a soft recovery material similar to a slow-recovery, resilient deformable material. A slow recovery material of this type is described in U.S. Pat. No. Re. B 29,487 which describes an ear plug in a form of a cylinder that can be squeezed to a small diameter in the wearer's hand, and then inserted into the ear canal where it expands to form a tight fit against the walls of the ear canal. Applicant has found such material, which can be made in various degrees of softness depending upon the amount of plasticizer that is used, to be an especially good noise-attenuating material. A very soft foam material has the advantage of being able to fit closely against the walls of the ear to avoid air gaps through which sound can pass. However, such soft foam material has the disadvantage of poor sound attenuating characteristics. A stiffer foam material is more difficult to deform to seal against the ear, but it has better noise attenuation for sound that passes through it.

It is possible to use moderately stiff foam material to obtain good attenuation for sound passing therethrough, and to provide good sealing against the walls of the ear, by pressing the cap 20 with substantial force against the ear. However, while the average person does not mind the application of a considerable force such as one pound during a short period of time, a force of substantially more than about 8 ounces applied for an extended period of time, such as more than a few minutes, becomes uncomfortable. Applicant utilizes a slow recovery material such as of the general type described in the above reissue patent, but with the amount of plasticizer limited to provide moderate stiffness. The stiffness is chosen so that when a large force such as 16 ounces is applied to the cap to deform it closely against the ear, or in other words to seat it against the ear walls, then the cap will retain the seated configurations so long as a moderate force such as 7 ounces continues to be applied to the cap. The band 12 is constructed so that it applies a continuous inward force of about 7 ounces when moved to its use configurations such as shown in solid lines in FIG. 1.

A wearer uses the apparatus by placing the band 12 around his head and with the caps 20 of the ear protectors lying against his ears. He then presses inward on both ends 18 of the ear band with sufficient force, such as about one pound of force, until he senses that the caps have been seated by noticing a reduction in outside noise. The wearer then removes his hands, so that only the continuous force of about 7 ounces is applied to the caps to keep them in their seated configuration and position. The apparatus can then be worn for an extended period such as an hour or more, without discomfort being experienced by most people. The apparatus can be easily removed and reinstalled on the ears in the same manner as for the original installation.

The coupling 22 shown in FIG. 3, includes a first body 32 of moderately resilient material such as a solid rubber, and a second body 34 of very soft, or resilient material, such as a soft foam material, that is bonded to the cap. The soft foam body 34 of a thickness of at least one-eighth inch permits tilting of the cap 20 to better fit against the ear. For example, in FIG. 5, the soft second body 34 is shown deformed slightly to permit the axis 36 of the cap 20 to be tilted by a few degrees from the axis 38 of the end of the headband. The coupling 22 had a central hole 40 (FIG. 3) which can receive a barbed rod 42, or rod with an enlarged head, that projects from the end of the headband. The end 18 of the band includes a plate-like outer portion 44, a post 46 extending inwardly from the outer portion by a small distance which is less than a centimeter, and a plate-like inner portion 48 at the inner end of the post. The ear protector 14 mounts on the barbed rod 42 and abuts the inner portion 48.

The form of the cap 20 as a thick sheet or plate, help to conform it to the orientation and shape of the ear. The sheet-like outer portion 24 has enough thickness, such as a 3/16 inch or 5 mm thickness, to enable it to deform about irregularities in the ear walls that immediately surround the ear canal while maintaining a seal. The thickness is also small enough, that the outer cap portion 24 can tilt slightly along with the coupling body 34 to the orientation of the ear walls. The cap 20 has an outer diameter D (FIG. 3) of about 2 cm, and the base of the protuberance E has a diameter of about 1 cm.

The ear protector 14 is a low cost replaceable device, so it can be replaced when it becomes soiled or when a new person is to wear the band 12. Replacement is accomplished by pulling off the old ear protector 14 to withdraw it from the barbed rod 42, and pressing a new ear protector onto the barbed rod, so it is held in an interference fit therewith.

Caps 20 have been constructed by dip molding an armature that fits into a central hole 50 at the outer face of the cap to form a cap of substantially constant thickness, or in other words, a sheet or plate-like shape. A soft recovery material constructed of 100 parts Geon 128, 95 parts Admex 523, 8 parts SD 200, 2 parts Stanclear Key 876, 0.5 parts VS 103, 3 parts Vanstay 8014, and 10 parts color and fire retardant has been used. This material has been found to become seated when a moderate force such as one pound is applied to force it against the ear, and has been bound to maintain its seating configuration and position when a force such as about 7 ounces is continually applied to the cap after it has been seated. The band 20 was constructed to apply about 7 ounces of force when the ear protectors 14, 16 were separated by about 4 inches. The band 20 was constructed of a resilient material such as a solid vinyl plastic, with a bent middle portion 12m, which brought the caps together with substantially no force on each other, as shown at 10A, when no separating force was applied to the band ends. This provided an almost uniform force of about 7 ounces when the band was expanded to a cap separation of about 3½ to 4½ inches to accommodate heads of different widths.

The soft or slow recovery material used by applicant is formulated primarily to retain its deformation when a lower force is continually applied, than was initially applied to cause the deformation. Applicant prefers to use a moderately stiff foam because it has better noise attenuation than softer foams. Such moderately stiff foam will more rapidly return to its original configuration than soft foam; therefore, it may be unsuitable for earplugs that are squeezed to a small diameter, and which must have a slow recovery when released to provide time to insert in the ear canal. However, in the present band earplug no such complete release occurs so such slow recovery is not necessary.

Thus, the invention provides an ear protector apparatus which includes an ear protector that can be worn comfortably, which fits closely against the ear to seal against the passage of sound through air gaps, and which is itself highly attenuating to sound passing therethrough. The apparatus includes a headband and a pair of ear protectors mounted at opposite ends of the band, with each ear protector including a cap that can seal against the ear. The cap is in the form of a thick sheet with a dish-shaped outer portion and with a tapered protuberance at the center, so the protuberance can fit into the outer end of an ear canal while the dish-shaped outer portion can seal to the ear walls lying immediately about the ear canal. The cap can be formed of slow recovery material to provide effective sealing with low sustained pressure. A good sound-attenuating soft or slow recovery material can be utilized by forming it so it seats when pressure above ten ounces is initially applied, and which maintains seating when a relatively low pressure such as 7 ounces is continually applied after seating has been accomplished.

Although particular embodiments of the invention have been described and illustrated herein, it is recognized that modifications and variations may readily occur to those skilled in the art and consequently, it is intended that the claims be interpreted to cover such modifications and equivalents.

What is claimed is:

1. An ear noise protector apparatus, comprising:
   a resilient head band having a pair of ear protector holders positioned to lie by the opposite ears of a person when the band lies about the person's head; and
   a pair of ear protectors mounted on said holders, each protector including a cap formed of a slow recovery, resilient deformable material, and said cap having a width greater than the width of a typical human ear canal, so a portion of the cap can lie against the walls of the ear that surround the outside of the ear canal;
   said slow recovery material being soft but being stiff enough that it prevents its full sound-sealing deformation against the ear walls unless an initial force of over 12 ounces is applied to the cap to deform it against the ear walls, but which retains its sound-sealing deformation so long as a predetermined sustained force which is less than 8 ounces is applied;

said band being constructed to apply said predetermined sustained force but no more than 8 ounces to said holders when the protectors thereon engage the ear, whereby a person can briefly apply a large force to seat the caps and thereafter the band holds the caps in their deformed state.

2. An ear protector, comprising:

a pair of caps of foam plastic, each having a convex face, and having a middle and a tapered protuberance at the middle that projects from the convex face, said protuberance having a diameter of about one centimeter at the base of the protuberance to substantially match the outer end of the ear canal but the protuberance being tapered so it does not hold itself in the ear canal; and a band which has opposite ends that hold said caps, said band pressing said caps toward each other with a force of about 7 ounces when the caps are pressed against the opposite ears of a person;

said caps each formed of a slow recovery resilient foam material which is chosen so each cap seats against an ear only when the caps are pressed together with a force of more than 12 ounces, but which remain seated when the force of only said band continues to press the caps against the ears.

3. An ear noise protector apparatus, comprising:

a resilient head band having a pair of ear protector holders positioned to lie by the opposite ears of a person when the band lies about the person's head; and a pair of ear protectors mounted on said holders, each protector including a cap formed of a slow recovery, resilient deformable material, and said cap having a width greater than the width of a typical human ear canal, so a portion of the cap can lie against the walls of the ear that surround the outside of the ear canal;

said slow recovery material being soft but being stiff enough that it prevents its full sound-sealing deformation against the ear walls unless an initial force of over 12 ounces is applied to the cap to deform it against the ear walls, but which retains its sound-sealing deformation so long as a predetermined sustained force which is less than 8 ounces is applied;

said band being constructed to apply said predetermined sustained force but no more than 8 ounces to said holders when the protectors thereon engage the ear, whereby a person can briefly apply a large force to seat the caps and thereafter the band holds the caps in their deformed state;

said ear protector includes a coupling lying between said cap and holder of said band, said coupling including a first body of moderately resilient material nearest said holder and a second body of very resilient material which is more resilient than said first body and which lies between said first body and said cap, to permit the cap to be tilted to more completely engage the ear walls.

4. An ear protector which can be mounted on a band device that urges it against the ear, comprising:

a cap of foam plastic, having a convex face and an opposite face and having a middle and a tapered protuberance at the middle that projects from the convex face, said protuberance having a diameter of about one centimeter at the base of the protuberance to substantially match the outer end of the ear canal; and a coupling of resilient material having one end attached to said opposite face of said cap and an opposite end attachable to a band device, said coupling including soft foam material having a thickness of at least one-eight inch, whereby one side of the foam can be compressed to permit tilting of the cap.

* * * * *